(12) United States Patent
Weinman, Jr.

(10) Patent No.: US 6,658,455 B1
(45) Date of Patent: Dec. 2, 2003

(54) METHOD AND SYSTEM FOR AN ENHANCED NETWORK AND CUSTOMER PREMISE EQUIPMENT PERSONAL DIRECTORY

(75) Inventor: Joseph Bernard Weinman, Jr., Basking Ridge, NJ (US)

(73) Assignee: AT&T Corp., New York, NY (US)

( * ) Notice: Subject to any disclaimer, the term of this patent is extended or adjusted under 35 U.S.C. 154(b) by 0 days.

(21) Appl. No.: 09/475,289

(22) Filed: Dec. 30, 1999

(51) Int. Cl.⁷ .............................................. G06F 15/16
(52) U.S. Cl. ...................... 709/203; 709/213; 709/218; 709/223; 705/2; 705/3; 345/970.1
(58) Field of Search ................................ 709/203, 201, 709/202, 218, 223; 379/88; 370/218; 707/10, 4, 104.1

(56) References Cited

U.S. PATENT DOCUMENTS

| | | | |
|---|---|---|---|
| 4,734,931 A | | 3/1988 | Bourg et al. |
| 4,800,582 A | | 1/1989 | D'Agosto, III et al. |
| 4,839,919 A | | 6/1989 | Borges et al. |
| 5,204,894 A | * | 4/1993 | Darden .................... 379/88.03 |
| 5,502,761 A | | 3/1996 | Duncan et al. |
| 5,509,049 A | | 4/1996 | Peterson |
| 5,764,731 A | | 6/1998 | Yablon |
| 5,940,493 A | * | 8/1999 | Desai et al. ................. 379/260 |
| 5,943,410 A | * | 8/1999 | Shaffer et al. .......... 379/213.01 |
| 5,946,684 A | * | 8/1999 | Lund ........................... 370/384 |
| 5,956,637 A | * | 9/1999 | Ericsson et al. ............. 455/414 |
| 5,978,806 A | * | 11/1999 | Lund ............................ 707/10 |
| 6,005,927 A | * | 12/1999 | Rahrer et al. ................ 379/140 |
| 6,018,568 A | | 1/2000 | Furman et al. |
| 6,091,808 A | * | 7/2000 | Wood et al. ................. 370/352 |
| 6,134,450 A | * | 10/2000 | Nordeman ................... 455/517 |
| 6,269,337 B1 | * | 7/2001 | Desmond et al. ......... 704/270.1 |
| 6,373,926 B1 | * | 4/2002 | Foladare et al. .......... 379/88.13 |
| 6,374,245 B1 | * | 4/2002 | Park ............................ 707/10 |
| 6,421,672 B1 | * | 7/2002 | McAllister et al. ............ 707/10 |
| 6,473,612 B1 | * | 10/2002 | Cox et al. .................... 455/414 |

* cited by examiner

Primary Examiner—David Wiley
Assistant Examiner—Phuoc Nguyen (57) ABSTRACT

Method and system for providing a personal network directory comprises terminal apparatus including a processor, memory and a keyboard for communicating with a network server. The network server may maintain a personal network directory for a telecommunications subscriber of called and calling party telephone numbers to/from the subscriber and identification of applications software which may be periodically updated. The subscriber may access the personal directory for a telephone number from a dumb telephone more quickly and easily than a shared directory assistance operator by dialing a special unique sequence of digits after a shared number such as 411 or (area code) 555-1212 or by dialing a unique character string for their personal directory. If the user has an intelligent telephone, the subscriber may via a communications protocol access and download one or more telephone numbers or programs at a time consistent with a personal rule-base associated with the directory in network or terminal memory.

3 Claims, 6 Drawing Sheets

FIG. 1    PERSONAL NETWORK DIRECTORY SERVICE ARCHITECTURE

FIG. 5

METHOD AND SYSTEM FOR AN ENHANCED NETWORK AND CUSTOMER PREMISE EQUIPMENT PERSONAL DIRECTORY

FIELD OF THE INVENTION

The present invention relates to the field of personal communications, and more particularly, to a method, apparatus, system and protocol for a network personal directory and a customer premise equipment (CPE) personal directory for storing, uploading and downloading data and executable programs.

BACKGROUND OF THE INVENTION

Currently, there is vast growth in emerging technologies that permit users to upload and download data and/or programs from, for example, the Internet or other sources into their personal computers (PCs) or other communications devices. Accordingly, users are able to access and retain such data and/or programs for personal use at anytime in the future or store a copy in the network for subsequent download, distribution or as a backup. For example, a user may be able to download applications, games, and information for personal use. This permits users to easily obtain programs and/or data or update their existing programs and/or data.

In addition, users are able to receive and store information in their personal telephony CPE devices such as pagers, wired and wireless telephones including cellular and digital telephones, handheld communication devices, personal computers and any other suitable devices for receiving and storing information. Thus, information such as paging messages, stock quotes, sports scores, and/or e-mail messages can be received and stored in the pager and/or cellular and digital telephones. Accordingly, users are able to access and retain such data and can view it at any time in the future.

Currently, users are unable to download, for example, personal directories, applications, operating systems and/or games into, for example, their cellular and/or digital telephones. For example, currently, users are unable to upgrade their existing telephony CPE to take advantage of additional features that may be available. For example, a user may want to upgrade to new operating systems, calculators, calendars, additional ringing tones, games and a variety of other suitable data and/or programs that can increase the functionality of their telephony CPE. Currently, if a user desires these additional features, the user must incur substantial additional costs for a new device even though their current telephone circuitry can support the additional features. Thus, present systems are disadvantageous in that they do not permit a user to download the desired features and/or data into their communications device.

In addition, the user may want to maintain an information database or directory list for a personal user, such a directory list having names and phone numbers of frequently called parties. Using current systems, a user may verbally request such telephone numbers of a called party from, for example, a directory assistance operator. In the alternative, the user may have previously stored the telephone numbers of the frequently called parties in their telephony CPE, electronic directory, or a conventional written notebook directory where the user has previously noted the numbers of called parties. To retrieve the telephone number from directory assistance, the user will likely sustain a charge from the provider of the service and/or the telecommunication service provider and will spend additional time in doing so. Once the number is retrieved, the user generally has the option of being automatically connected to the called party, via directory assistance at an additional charge, or hanging up and dialing the retrieved number. Unfortunately, the mapping between one or more common names, for example, "Joe's Pizza Parlor," or "Mom," or "the Italian restaurant near the mall," and the telephone number is lost unless either the user memorizes, manually records, or manually loads the retrieved name and number into the CPE, written notebook or other device. Loading this number into a personal communications device or electronic directory currently requires a sequence of keystrokes immediately after the telephone number is obtained or after the call is terminated. This may be difficult for the user if the user is, for example, driving or in a meeting or otherwise unable to save the telephone number. In addition, using conventional techniques, saving such numbers can be time consuming and is typically not the user's highest priority at that moment, and therefore likely to be deferred and likely forgotten. If the user fails to record this telephone number, the user may likely have to access directory assistance again to retrieve the called party number and be assessed additional charges and/or expend additional time. Even if the user records the telephone number, should the telephone number or the area code change, the number will become invalid.

U.S. Pat. No. 5,204,894 to Darden describes a Personal Electronic Directory (PED), where subscribers may call a special number to access their PED to store and retrieve names and telephone numbers. According to this patent the subscriber must call the special number and manually store the name and number into their PED. In other words, rather than "manually" writing an entry into a paper directory, Darden teaches a method for "manually" entering their number into their PED. However, similar problems exist, for example, mis-keying entries and/or forgetting to enter numbers into their PED. If the number has been manually entered previously, the subscriber can later access their PED to retrieve the previously stored number when required. Darden teaches a complicated flow of keystroke entries to store and access previously stored telephone numbers.

The system of Darden is disadvantageous in that it requires a user to call a special directory access number prior to manually storing and/or retrieving numbers from their personal directory. This additional step increases the difficulty in using the personal directory and increases the amount of time the user will spend completing the desired call. Further, if the user loses or is otherwise unable to recall the directory access number, the user will be unable to access their personal directory.

U.S. Pat. No. 5,764,731 to Yablon describes a system for delivering telephone numbers to a primary user's telephone memory, such that the stored number can then be employed directly by the primary user for later memory redial of that number. The system utilizes a handshake/signal manager having the hardware and/or software to permit remote downloading of the telephone's memory by a variety of remote number sources. The telephone number is entered into the telephone's memory, not by the primary user but by a user or server device physically removed from the primary user's telephone. The telephone locally stores the telephone number along with the other information identifying the called party, thus the numbers can be used directly from the phone's memory for recall and signalling purposes.

The system disclosed in Yablon is disadvantageous in that all the directory information is stored locally in the primary user's telephone. Thus, in the event the primary user loses or upgrades to another telephone all information residing in the first telephone is lost. Further, where the primary user has, for example, a wireless phone, a work phone and/or a home phone these independent devices are unable to share the plurality of locally residing information described in the system disclosed in Yablon.

Thus, there is a need for a method and system that permits users to download applications, operating systems and/or data into their telephony CPE for enhanced functionality and capabilities. There is also a need for intelligent telephony CPE (terminal apparatus) that is able to download from, or upload to a network, or copy to or from other devices, and run desired executables and/or data for enhanced functionality and capabilities. There is also a need for a personal network directory that can be updated and accessed automatically without a manual user interface step. There is also a need for a system and protocol that monitors a user's dialing habits and/or preferences, using predefined personal communication devices, to automatically update the user's personal network directory and monitor user preferences to provide personalized information to the user. Thus, there is a need for a personal replicatable network directory for telephone CPE that tracks and shares work and/or personal information so that information is available to the user at any time.

SUMMARY OF THE INVENTION

The present invention is directed to a method, system, protocol and apparatus for maintaining a personal network directory (PND) permitting a user and subscriber to store applications, operating systems and/or data for use via their personal telephony CPE, or for access via shared or publicly accessible devices. More significantly, the present invention overcomes the shortcomings of existing systems described above by providing a simple and user friendly methodology for permitting subscribers to maintain and use, for example, a personal directory list and/or upgrade data and/or upgrade features in their telephones.

The serving network or related networks may automatically preserve a personal history of telephone calls for either parties calling the user, calls from the personal communications device recording telephone numbers for callers and callees, or requests for directory assistance. The network can access related databases to retrieve or store locally further information about the caller, for example, caller preferences or callee, for example, name, telephone number and location. There may be a protocol established between the network and the subscriber's personal communications device whereby a subscriber, such as one having a cellular telephone, can immediately access and download a needed telephone number such as that for their doctor without entering any directory access code or access number. The protocol may constantly monitor the subscriber's calling habits to update, append and/or permit automatic access to the subscriber's PND. The subscriber may further be able to predefine a plurality of terminal devices that may be similarly monitored in accordance with the protocol and have the ability to automatically share a common or related PND. In addition the subscriber may have a credit card, calling card or code to activate the communications protocol from any phone or customer equipment. Accordingly, the subscriber may have a single location for storing, for example, information for all parties the subscriber may communicate with either on a regular and/or less than regular basis. For security and/or privacy, the subscriber may be able to partition the directory so as to limit access to desired portions of their network directory and/or create multiple subsets of their directories that may be used by coworkers and/or members of the subscriber's family. The stored information may include, for example, names, numbers, e-mail addresses, Uniform Resource Locators (URLs) and physical addresses of business associates, friends, relatives and/or local shops the subscriber usually frequents. A subscriber may be able to customize and personalize a plurality of rule sets to control the flow of information into and out of their PND. At the same time, the developed communications protocol and circuitry of a terminal device for a subscriber may be adapted to receive network software updates for consistency with the network, games, number or address changes of individuals or businesses, or any other kind of software and/or data updates conceivable.

One object of the present invention, then, is to permit a subscriber to download into a personal communications device, executable programs and/or data to enhance the functionality and capabilities of the CPE without purchasing a new device.

Another object of the present invention is to provide an apparatus, method, system, and protocol that simplifies, optimizes and synchronizes how a user can download, maintain, upload, and migrate data from updated personal directory having a variety of information. Accordingly, the system and protocol may be activated for operation every time the subscriber goes off hook, attempts to communicate using a plurality of pre-defined terminal devices or CPE and/or in the background while the CPE is in, for example, a standby mode, as in the case of a wireless device which is on, but not engaged in a specific call. The subscriber's calling habits, preferences and/or activities while using the plurality of pre-defined terminal devices may be constantly monitored to maintain a single PND containing, for example, a single personal directory list (PDL) that may be appended or accessed automatically without manual entry of any directory access number. The PDL may be stored in the network and/or copies, or differing views or subsets of the network PDL may be downloadable directly into the subscriber's personal communication device, terminal or CPE. Accordingly, the subscriber may have access to the data stored in, for example, their PDL current as of the moment of the last download even if the subscriber subsequently ventures outside their service territory or is otherwise in a location where access to their PND is not possible. Note that the CPE whose PDL is updated may differ from the one from which the call is placed. For, example, a call placed from a payphone, wherein the call is identified by the calling card or like means, may result in the PDL of a distant cellular telephone being updated accordingly.

In yet another embodiment, the user's communication device is dumb and the network may be accessed and controlled from such a dumb telephone to access telephone numbers and the like for the user. Here the personal directory may be analogized to a network based bookmark list and log where the user from the "dumb" telephone may bookmark telephone numbers by appropriate command to the network when the user places the call, gets directory assistance or immediately upon receiving a call.

These and other aspects of the invention will become clear from the following detailed description and the drawings.

BRIEF DESCRIPTION OF THE DRAWINGS

The present invention will now be described in more detail with reference to preferred embodiments of the invention, given only by way of example, and illustrated in the accompanying drawings in which.

DETAILED DESCRIPTION

The principles of the present invention are illustrated in several exemplary embodiments which provide an apparatus, method, system and protocol for copying data and/or executable programs into a network personal directory as well as downloading, or uploading, or migrating data and/or executable programs in to a personal communication device and/or CPE or for temporary usage by the CPE.

Figure 1:
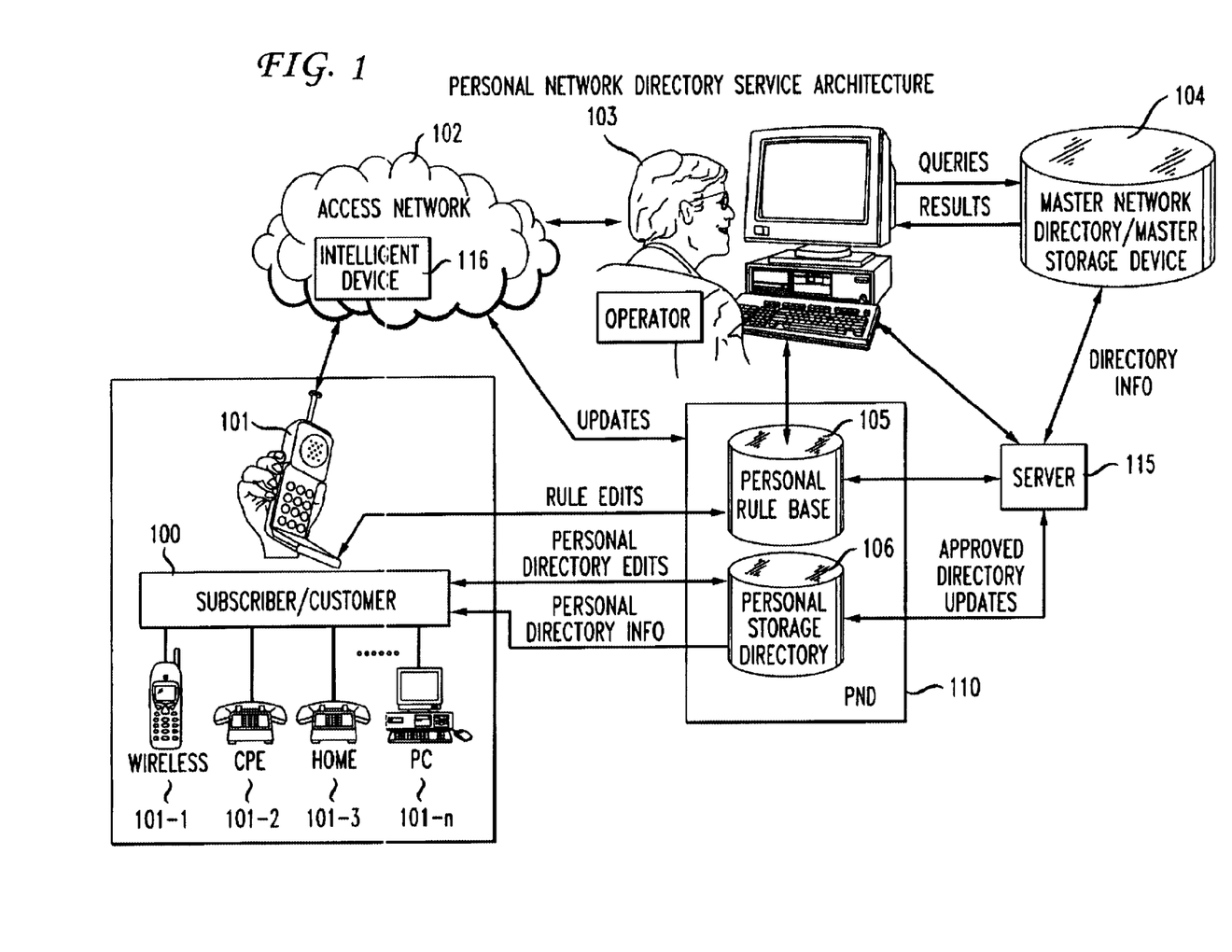
FIG. 1 illustrates an embodiment of the present invention.

FIG. 1 illustrates an embodiment of the present invention. A customer or subscriber 100 of a personal network directory service may contact, for example, a human or machine operator 103 or intelligent voice response unit (VRU) responsive to voice and/or key command via telecommunications access network 102 to retrieve the desired information and/or executables. The subscriber 100 may contact the operator 103 via any suitable CPE 101, which may be "dumb" (no inherent processing capability) or intelligent (have processing capability). Although a wireless telephone is shown, the CPE 101 may be any communications device, for example, a cellular telephone, a digital telephone, a personal communications device, a land-line telephone, a personal or lap top computer, a video telephone, a one-way or two-way pager, a pay phone and/or any other suitable one way or two way communications device and/or system. It is to be understood that CPE as used herein denotes any communications devices, that may be located at a customer's premises or, in the alternative, the device may be located at a remote location. In embodiments of the present invention, the subscriber 100 may predefine a plurality of devices (CPE 101), for example, a wireless phone 101-1, a work phone 101-2, a home phone 101-3 and/or up to a personal computer 101-n that the subscriber may desire to utilize to access a PND 110 (to be described below in detail). In alternative embodiments of the present invention, the subscriber 100 may use a calling card, a credit card, a phone number or code from any other device, for example, a pay phone or other public phone, to automatically access their PND 110 and/or to activate a communications protocol (to be discussed below in detail). Access to the PND may include any security and/or authentication system known to those skilled in the art to prevent unauthorized access to the PND. In yet alternative embodiments of the present invention, the subscriber 100 may predefine a plurality of additional devices, for example, a plurality of wireless phones to have access to the PND 110. These may be, for example, additional phones for the subscriber's wife, kids, co-workers and/or other defined groups, for example, bowling clubs or professional associations. As will be discussed below in more detail, the subscriber 100 may by data partitioning and/or mirroring partition the single PND 110 to control and/or limit access to the PND 110 by the additional users.

The telecommunications access network 102 may include a plurality of differing networks, for example, a local, national, international telecommunications network, a paging, cellular, or PCS network, an Internet, cable television and/or any other suitable networks. While the embodiments described below relate to communications networks including a cellular phone system, a PSTN, a broadband network, a CATV network, an SS7 network, a satellite network, Internet or a wireless Centrex system, it is to be understood that the present invention can be applied to all types of communications systems.

Referring again to FIG. 1, the operator 103 may be, for example, a directory service operator 103 who can be reached by dialing, for example, 411, *411, (NNN)-555-1212 (where NNN represents the area code of the desired number), a shorthand version thereof for those who subscribe to the service of the present invention, double zero (00) operator local and national directory assistance or any other suitable number available for accessing directory or other operator assistance. The directory assistance operator 103 may be local, or may be located in another city, state, and/or country. In alternative embodiments, the operator 103 may be a customer service representative for a corporation providing the downloadable data and/or programs or may be may be any other individual or entity desirous of sharing information. The customer service representative may be reached by dialing an appropriate number provided by the corporation for the provided services. Accordingly, the customer service representative 103 may provide, for example, other data, programs, and/or executables the customer 100 may want to down load into their CPE 101, PND 110 or have temporary access to. The downloadable data and/or executables for storage or for temporary use may include, for example, single telephone numbers or whole personal directory lists, entire residential or business directories for a country, state, city and/or town, e-mail addresses, URLs, postal addresses, applications, operating systems, games, calculators, calendars, additional ringing tones, and a variety of other suitable data and/or programs that can increase the functionality and/or utility of CPE 101. It is to be understood that the present invention is not limited to only downloading data and/or executables, and may be utilized for uploading data and/or executables to/from a network and/or other devices. In alternative embodiments of the present invention, the operator 103 may automatically become a personal assistance operator by dialing or otherwise specifying a personal access code or other unique identifier. In embodiments of the present invention, the customer, if a subscriber, may access the service of the present invention directly by dialing a unique service access code (unique to the service) and a personal identifier and/or a security code or password as will be further explained herein, or any other known method. For example, if the subscriber 100 has a cellular or digital phone manufactured by, for example, Nokia Corporation or utilizes AT&T Corporation's network for communications, the subscriber 100 may be given a unique service access number by, for example, Nokia Corporation and/or AT&T Corporation to download or upload and access data, programs and/or other executables to, for example, upgrade and increase the functionality of their device 101. The subscriber may have access to such information, for example, on a one time, transactional, or a traditional ongoing subscription basis, for a fixed period of time, for a fixed number of updates, or other terms and/or conditions. The information may be, for example, downloaded or uploaded for temporary storage, migrated into existing data, migrated to another CPE, and/or permanently archived. In alternative embodiments, a unique subscriber identifier, for example Automatic Number Identification (ANI) or unique personal identifier may be used to permit downloads.

In a preferred embodiment of the present invention, a protocol (to be described below in detail) may be established between the subscriber's 100 CPE 101 and the network 102, for example, every time the subscriber 100 goes off hook, attempts to complete a call, receives an incoming call and/or in the background when the CPE 101 is in use and/or on standby. In embodiments of the present invention, the communications protocol may be activated while the CPE 101 is connected to the network or, alternatively updates may be made directly to a PND 110 even if the CPE 101 is not currently connected to the network. Thus, when a subscriber 100, for example, attempts to make a call or even in the background while the CPE 101 is in standby or in use, there may be some handshaking between the subscriber's 100 CPE 101 and an intelligent device 116 that may be located within the access network 102. The intelligent device 116 may be, for example, an intelligent switch having the ability to communicate with the subscriber's 100 CPE 101, the PND 110, operator 103 and/or any other device and/or individual to establish the communications protocol. In embodiments of the present invention, the intelligent device 116 may exchange information with the CPE 101 on a constant basis to automatically provide new information and/or applications that may become available. Accordingly, the handshaking may establish the protocol that monitors the subscriber's 100 activities to, for example, download and store the desired information in the subscriber's 100 PND 110 automatically.

As already introduced, in alternative embodiments of the present invention, an automated device 103 may replace a live operator to receive calls from subscriber 100 and provide the requested information without human intervention. The automated device may include a voice response unit (VRU) (not shown), a dual tone multi frequency (DTMF) receiver (not shown) and/or any other suitable resources for receiving inputs from the subscriber 100 and providing the requested information. The automated device may have a human operator standing by in the event the device is unable to complete the customer's 100 request. The operator 103 may query, for example, a master storage device (MSD) 104 to retrieve, for example, the data and/or executables requested by the subscriber 100. In embodiments of the present invention, the MSD 104 may include a master network directory listing and/or database containing the names, addresses and telephone numbers (e-mail addresses and/or URLs in an Internet embodiment) for all customers, businesses and/or residents in the relevant city, state and/or country. The MSD 104 may be co-located with the operator 103 or, in the alternative, may be located at a remote location. In embodiments of the present invention, the MSD 104 may be a distributed database that may physically be located in a plurality of places but may virtually act as a single database. The MSD 104 may be owned by the corporation providing the data and/or executables and permits operator 103 access or, in the alternative, the MSD 104 may be owned by a network carrier or a local service provider and may permit the storage of data and/or executable from a plurality of sources. In alternative embodiments, the MSD 104 may provide without human intervention automatic downloads or uploads to the subscriber's 100 CPE 101 via server 115 (discussed below in more detail) and access network 102 utilizing the established protocol, established earlier.

As already introduced and shown in FIG. 1, the subscriber may have a PND 110. Preferably the PND 110 resides outside of the subscriber's 100 CPE 101 in, for example, the access network 102. In alternative embodiments, the PND 110 may reside within the CPE 101. The PND may include a personal storage directory (PSD) 106 for storing data, programs, applications, games and/or any other executables the subscriber 100 may require. The PSD 106 may be located outside the PND 110 in, for example, the subscriber's CPE 101. The PND 110 may also include, for example, a personal rule-base 105 (to be described below in detail) for regulating information provided to the subscriber 100.

As discussed above, the subscriber 100 may have a personal rule-base 105 that may regulate information provided to the subscriber 100. In embodiments of the present invention, the personal rule-base 105 may reside in the subscriber's 100 CPE 101 or, in the alternative, may be located external to the CPE 101 in, for example, the PND 110 which is located in the network 102. The subscriber 100 may be able to edit and/or update rules in the personal rule-base 105 directly from their CPE 101 or, in the alternative, request the assistance of the operator 103 for modifications. In the event the rule-base 105 resides in the subscriber's 100 CPE, the operator 103 may utilize the established protocol between the operator 103 and the CPE 101 for updates to the rule-base 105.

The rule-base 105 may determine whether the information requested by the subscriber 100 has been approved to be stored, for example, in the PSD 106 owned by the subscriber 100 either in their devices or in the network. As indicated earlier, the PND 110 may include both the personal rule-base 105 and the PSD 106. Accordingly, the PND 110 may reside outside the CPE 101 in, for example, the network 102. The PDL 152 may reside in the PSD 106 located within the PND 110 in the network 102. In one embodiment, the rule-base 105 may control which information is downloaded into a Personal Directory List (PDL) 152, shown in FIG. 1A. The PDL 152 may contain information for all parties the subscriber may communicate with, for example, the names and numbers of all residences and/or business called by the subscriber. The PDL 152 may include, for example, names, numbers, e-mail addresses, Uniform Resource Locators (URLs) and/or physical addresses of business associates, friends, relatives and/or the local shops the subscriber usually frequents and/or any other suitable information the subscriber intends to store in their PDL 152. Based on the size of the PSD 106, the subscriber 100 may request the operator 103 to down load an entire residential and/or business listing for, for example an entire corporation, town, city, state and/or country.

Figure 1A:
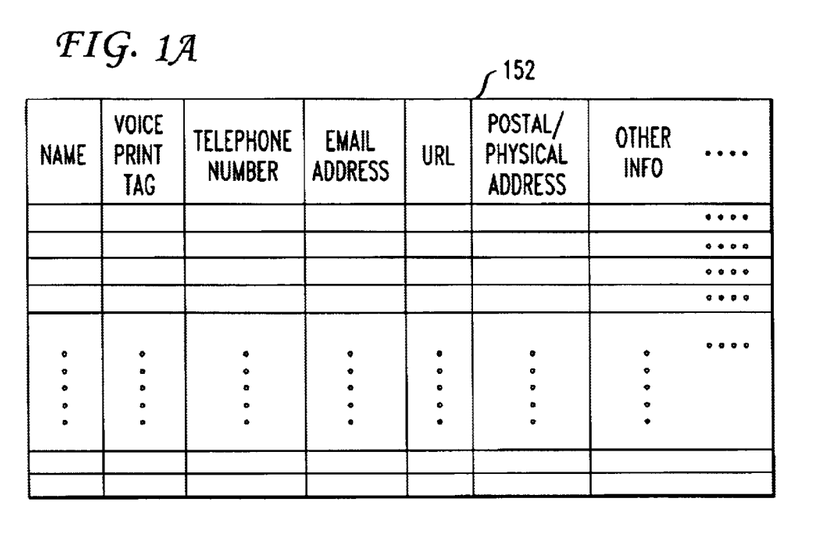
FIG. 1A is an embodiment of a personal directory list in accordance with the present invention.

Under embodiments of the present invention, the subscriber may be able to store a voice print tag corresponding to a listing in their PDL 152. When information is appended to the subscriber's 100 PDL 152 or to the subscriber's PSD 106, the subscriber may be prompted to append a voice print tag corresponding to the information. The voice print tag may be used to select an entry so as to, for example, add, retrieve, edit, or delete the corresponding information in the future. Accordingly, the subscriber may save the number for their mother, which may be stored in the PND as "Elizabeth Jones at 123 Elm Street," and add a voice print tag of, for example, "Mom." Thus the user may be able to retrieve the number by using the voice print tag at a later date. The voice print tag may be encoded and stored in, for example, the subscriber's PDL along with the corresponding information. The system in accordance with embodiments of the present invention may include a plurality of commands, for example, "add," "call," "edit," "find," "delete" or any other suitable commands that may be spoken by the subscriber 100 and recognized by the intelligent CPE 101 or by the subscriber's PND 110 in conjunction with the server 115. The system may use known voice recognition methods to recognize and effect the command. Thus, under embodiments of the present invention, the subscriber may combine the command with the voice print tag, for example, to complete a call to a called party. Thus, the subscriber may say "call Mom." A Voice Recognition Unit (VRU) in the CPE 101 or in the intelligent device 116 utilizing the communications protocol may recognize the command "call" and a central processor may attempt to find a match for the spoken word "Mom" with the previously stored and encoded voice print tag in the PDL. Once a match is found, the central processor may effect the recognized command, for example, "call" to the telephone number associated with the voice print tag and complete the call to "Mom". It is to be understood that the voice print tag is not limited to the telephone numbers in the subscriber's PDL 152, but may be used to download, execute, delete or edit any other information that may reside in the subscribers PSD, for example, the applications, games or other executables. In embodiments of the present invention, multiple voice print tags may index the same entry or alternatively, a single voice print tag may index multiple entries. For example, a single voice print tag may index and dial multiple telephone numbers. Accordingly, a subscriber may have two numbers for "Mom" stored in the PDL 152, for example, a work number and a home number. Accordingly, when the subscriber says, "call Mom," both numbers may be dialed simultaneously until one number connects, at which time the call to the other number may be terminated.

The PDL 152 may further include information the subscriber has downloaded from, for example, directory service operator 103. In one embodiment, the rule-base 105 for regulating information into PSD 106 may indicate that when the subscriber 100 requests, for example, a telephone number for a residence, then the subscriber's 100 PDL 152 should be updated with the name, number, e-mail address and/or any other information as designated in the subscriber's 100 rule-base 105. By private query and response, the subscriber 100 may edit the rule-base 105 to download information for all the, for example, local Chinese restaurants in their work, home and/or even current wireless phone area. Thus, for example, if the subscriber in an unfamiliar area and desires to know the name, number and location of restaurants in the area, then based on the location of the subscriber's, for example, cell or digital phone, this information may be delivered into the subscriber's PDL 152 via the rule-base 105, server 115 and MSD 104. Known systems may be used to determine the current location of the subscriber's 100 CPE 101. In yet other embodiments of the present invention, the rule-base 105 in conjunction with server 115 may be programmed to monitor the subscriber's 100 preferences. Based on the historical activity of the subscriber 100, the rule-base 105 may permit appropriate information to be downloaded into the PSD 106. If the subscriber 100 always updates the version of a software running in their CPE 101 or likes additional features for the CPE 101 or orders pizza, the subscriber's 100 PSD 106 may be downloaded with, for example, the new software or additional features or names of additional pizza place in the area. In embodiments of the present invention, the subscriber 100 may be able to enable or disable such auto-updates to their PND 110 and/or PDL 152.

In embodiments of the present invention, the subscriber 100 may pre-authorize the storing of any information that may be requested from an operator 103 into their PSD 106. In yet other alternative embodiments of the present invention, the rule-base 105 may regulate updates to the subscriber's PSD 106 on a per-transaction basis. For example, every time the subscriber 100 requests the assistance of the operator 103 to retrieve, for example, the number of a desired party or a higher version of the operating system or game for their CPE, the operator 103 may inquire whether the subscriber 100 would like the requested information appended to their PSD 106. In the event the subscriber 100 wants the number added to their PSD 106, the subscriber 100 may verbally notify the operator 103 or in the alternative, for example, press '1' to download the requested telephone number. In alternative embodiments, the personal rule-base 105 may regulate how executables and/or data may be down loaded to the subscriber's 100 CPE 101 for increased functionality or stored in the PSD 106 for subsequent temporary usage or for future downloading.

In embodiments of the present invention, contents of the PSD 106 may be entirely or selectively downloadable (i.e., portions of the PSD may be downloaded) into the subscriber's 100 CPE 101. For example, the subscriber 100 may desire that the information that currently resides in the PSD 106 of the PND 110 be downloaded into their CPE 101. Thus, by using the protocol established between the CPE 101 and network 102 via the intelligent device 116, the desired information may be stored within the CPE 101. Accordingly, if the subscriber 100 is in an area where access to the PND 110 is not possible, for example, when the subscriber 100 is outside the service territory of the wireless device 101-1, the subscriber 100 will continue to have access to the information that is contained in the PSD 106 current as of the date of the down load. The subscriber 100 may download or upload the entire contents of the PSD 106 or may select a portion of the information to be downloaded into their CPE 101. For example, the subscriber 100 may choose to only download the names and corresponding numbers of frequently called parties into their CPE 101. In the alternative, the subscriber 101 may choose to download all the names and numbers currently contained in their PDL 152 into their CPE 101. In yet alternative embodiments, the subscriber 100 may select the desirable operating systems, applications, games and/or other executables for downloading from their PND 110 into their, for example, wireless telephone 101-1.

In embodiments of the present invention, the data stored in the CPE 101 and/or in the PND 110 may be migrated between different devices. Using Personal Directory Migration (PDM) CPE 101 may be able to transfer stored data from one CPE to a different CPE. Accordingly, PDM may permit users to transmit, for example, one or more phone numbers and/or corresponding information, and/or selected portions of their PDL to another CPE, PND or any other device or location in the network. For example, if a subscriber's co-worker requires the name and number of a client, the subscriber can automatically transfer such information into the co-worker's CPE such that it may be automatically appended, in accordance with their rule base, into to their PDL and/or PND. In the alternative, such information may be provided for temporary storage within the other CPE and subsequently discarded after use. It is to be understood that, other information such as software and/or other executables may also be migrated or transferred between devices and/or the PND. For example, if the subscriber's CPE containing their PDL and/or other software is lost, stolen, broken or otherwise replaced, the subscriber may be able to transfer the entire or desired portions of their PDL or other information residing in their PND into their new CPE. In addition, if the subscriber desires to get a new CPE, the subscriber may transfer information directly to and/or from their old CPE into and/or from their new CPE. Note that the CPE whose PDL and/or memory is updated may differ from the one from which the call is placed. For, example, a call placed from a payphone, wherein the call is identified by the calling card or like means, may result in the PDL of a distant CPE, for example, a cellular telephone being updated accordingly.

Embodiments of the present invention may include a billing infrastructure to bill a subscriber 100 for downloading, for example, phone numbers, addresses or associated information, desirable operating systems, applications, games and/or other executables into their PND 110 or alternatively, directly into their CPE 101, for example, a wireless telephone 101-1. Embodiments of the present invention may cooperate with existing telecommunications and/or network infrastructure for, for example, billing services, administrative management, systems management, network management, etc. It is to be understood that the subscriber 100 may copy the desirable data or executable into a PND 110 for downloading or using at a later time. Accordingly, the subscriber may dial an appropriate service and may select or be notified about, for example, suitable software or executables available for downloading at a predetermined fee. The subscriber 100 may be informed that the particular software or executable can be downloaded at a predetermined fee that can be paid using, for example, a credit card, calling cards, added to the subscriber's monthly bill or separately billed directly to the subscriber. In alternative embodiments, the subscriber 100 may periodically and/or automatically be informed about new updates for the particular CPE 101 the subscriber has and the associated fees for such updates. For example, the subscriber 100 may be informed that new ring tones or games are available for their brand or type of wireless phone 101-1 at predetermined fee. The subscriber 100 may authorize download/copy the updates immediately or may defer the download/copy for a later time, for example, during an idle or standby period. Accordingly, the subscriber 100 may be billed appropriately for the desired or downloaded updates. The subscriber 100 may incur additional fees where the subscriber 100 desires to be kept up to date with new information or available executables for their devices 101. In alternative embodiments, the subscriber may receive updates for free or at a fee based on previous transactions (e.g., buy two get one free), at discounted rates based on usage and as a package that comes with the purchase of the CPE, software and/or service. In alternative embodiments, the subscriber may include a rule in their rule base that says, for example, automatically download all new ring tones that cost less than 25 cents or ask for authorization for all updates that cost more than 25 cents. Optionally, updates, as described above, maybe available to a non-subscriber at same or increased fees. The above described billing information as well as other required billing information may be managed in a personal configuration program file by server 115 (discussed below in more detail).

As introduced above, the personal rule-base 105 and PSD 106 may reside in the PND 110 that is subscriber specific and served by a server 115 which regulates information flow with operator 103 and/or directly with the MSD 104. The server 115 may be in communication with the operator 103, the MSD 104 and indirectly, according to FIG. 1, with the subscriber 100 in the present embodiment. In an alternative embodiment, the subscriber 100 may contact the server 115 directly, for example, via the Internet or dial-up data connection, for example, to do rule updates to rule-base 105.

According to the present invention and their personal rule-base 105, the subscriber 100 may receive updated versions of, for example, operating systems, games, and/or other suitable features for their CPE 101. The subscriber's rule-base 105, under server 115 control may automatically download the data and/or executables every time there is a new version without seeking the permission from the subscriber 100 or the intervention of operator 103. In the alternative, the subscriber's rule-base 105 may indicate that the subscriber should be asked whether a download is desired and/or be notified any time there is new version of, for example, an executable available for the subscriber 100 to download to their CPE 101. By private query and response, the subscriber 100 will have previously indicated the characteristics of CPE 101 to the personal rule-base 105, for example, the type of CPE, ability to play games, what games, what software from what company, and the server 115 can go look for the updates on a periodic basis and/or as a background task. Other background tasks may include, for example, updates to the subscriber's 100 PDL 152 by the server 115, on a periodic basis. For example, if the number, address or area code for a particular called party has changed the server may confirm and regularly update this information in the PDL so that the information is current. In the event the subscriber 100 has a plurality of devices, for example, the subscriber's wireless phone 101-1, work phone 101-2, home phone 101-3 and/or PC 101-n, the server 115 may interface with each device either automatically or based on the rule-base 105 information as previously provided by the subscriber 100. The server 115 may keep track of a plurality of characteristics associated with each device 101-1 through 101-n, for example, the type of device, current versions of software and/or hardware the device uses, preferences of the subscriber 100, the type of information that needs to updated periodically for a particular device, and/or any other suitable information. In alternative embodiments of the present invention, announcement of an update may be accomplished by, for example, the server sending a voice mail message to the subscriber 100 and permitting an automatic update if the subscriber 100 wants the information downloaded to their CPE 101, the server 115, optionally, having obtained the update ready for download for temporary storage in PSD 106. Consequently, PSD 106 is not just a repository of telephone numbers or e-mail addresses for subscribers but may also be a repository for application software updates ready for downloading to CPE 101.

Preferably, the PSD 106 may be stored within the PND 110 that is located external to the CPE 101, for example, in the local telecommunication network 102. In alternative embodiments, the PSD 106 may be located within the subscriber's 100 CPE 101. If the PSD 106 is located within the CPE 101, the requested telephone number, for example, may be downloaded directly to the CPE 101. In a preferred embodiment, where the PSD 106 is located in the network 102, the subscriber 100 may access the PSD 106 via the established protocol between their CPE 101 and the PND 110. Accordingly, the subscriber 100 may not need to enter any access code or identification. In alternative embodiments of the present invention, where the PSD 106 is located in the network 102, the PSD 106 may be secured for access only by the intended person via a personal identification through known means. As indicated earlier, the PSD 106 in conjunction with the server 115 may educate itself over time with signals from the subscriber 100 as to which telephone numbers to save, what software to update and the like and thus retrieve such number and software updates without prompting the subscriber.

As indicated earlier, in embodiments of the present invention, the subscriber 100 may predefine a plurality of additional devices, for example, a plurality of wired or wireless phones 101-1 to have access and share PND 110. These may be, for example, additional wired or wireless phones for the subscriber's wife, kids, and/or co-workers. Accordingly, a single PND may have a plurality of users as defined by the subscriber 100. Although it may be desirable for the subscriber 100 to own and maintain a single, synchronized and shared personal directory; doing so may create security and/or privacy concerns. In embodiments of the present invention, the subscriber 100 by data partitioning and/or data mirroring may be able to alleviate such security/privacy concerns. The subscriber 100 may create different security levels and/or ratings for the plurality of users of the shared PND. For example, the kids may have a security rating of a "5" (lowest), permitting access to only selected portions of the PND, while the subscriber 100 may have a security rating of a "1" (highest), permitting access to the entire database. The plurality of security levels may be created by partitioning the shared PND database and assigning the appropriate security levels for each user. The subscriber 100 may use data mirroring to create replicated copies of the PND that may be subsequently partitioned. In accordance with the above described features of the present invention, the subscriber may further create rules in rule base 105 to control how data may flow in and out the shared PND for each of the plurality of users of the shared PND. Optionally, the subscriber may permit each of the plurality of users to have different levels of functionality, for example, to change or update the rule base, to change CPE configuration, download executables, to block long distance calls, or prevent calls to certain called parties and/or other suitable features of the CPE and/or PND. In alternative embodiments of the present invention, for example, a password, PIN, or voiceprint (voice security access) may be created to permit segmented access to the PND.

Figure 2:
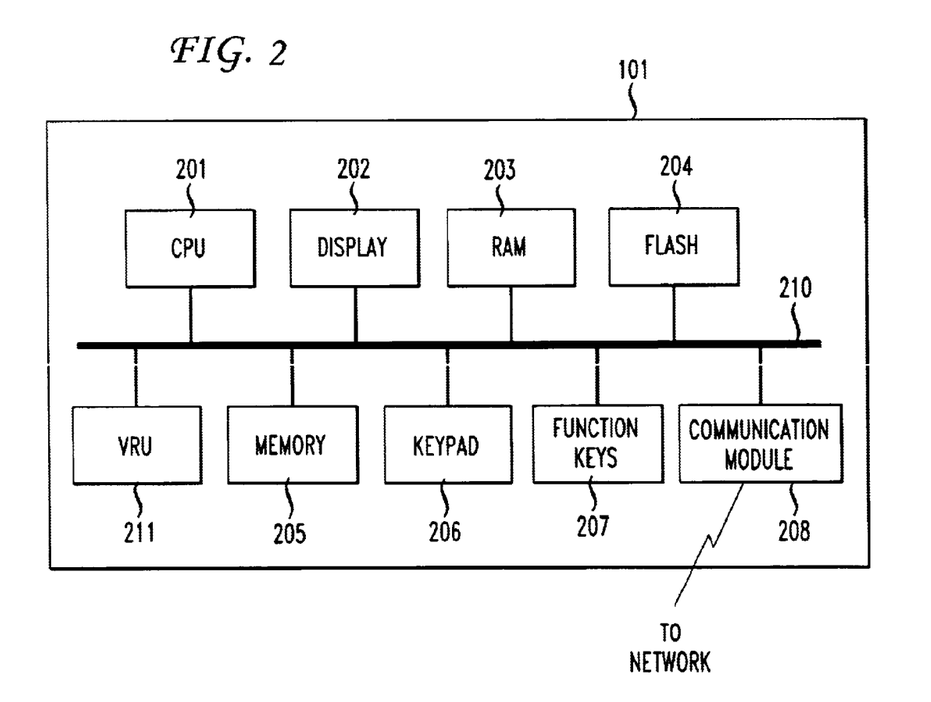
FIG. 2 is an embodiment of customer premise equipment in accordance with the present invention.

FIG. 2 is a block diagram of a CPE 101 in embodiments of the present invention. As indicated earlier, the CPE 101 may be any communications device, for example, a cellular telephone, a digital telephone, a personal communications device, a land-line telephone, a personal or lap top computer, a video telephone, a one-way or two-way pager, and/or any other suitable device and/or communications system.

Embodiments of the present invention may include at least some of the plurality of elements as illustrated in FIG. 2. These elements include, for example, a central processing unit (CPU) 201, a display unit 202, RAM 203, a flash unit 204, a memory 205, a keypad 206, function keys 207, a communications module 208, a system bus 210 and a VRU 211. It is to be understood embodiments of the present invention include, for example, a microphone, speaker, antenna (all not shown) and/or other suitable elements that may be desired for the desired operation. The system bus 210 may permit data transfer between the plurality of elements to permit, for example, the downloading, storage, and retrieval of desired data and/or executables. For example, when the PSD 106 resides in the CPE 101, the communication module 208, comprising at least a transmitter and a receiver, may communicate with the network 102 and receive the requested information from the operator 103 and forward this information for storage to the memory 205 via the system bus 210.

In alternative embodiments, when the PSD 106 resides with the PND 110 in the network 102, the communication module 208 may communicate with the PND 110 via the established protocol. The PND 110 may establish communications with the CPE 101 via the intelligent device 116 located within the network 102 and the communications module 208. As introduced earlier, the communications module 208 may establish the communication protocol as soon as the subscriber 100 goes, for example, off hook, or otherwise tries to use CPE 101 for communications and/or in the background while the CPE 101 is in use or on standby. The provided information from the operator 103 may be in the form of analog tones of varying frequencies or in the form of digital data. It is to be understood that embodiments of the present invention may utilize any of a variety of wired or wireless communications protocols known to those skilled in the art. The communications module 208 may receive the data from the operator or representative and the CPU 201 may process the data accordingly.

In embodiments of the present invention, the memory module 205 may store the PSD 106 or the PDL 152 and/or any other data or executables the subscriber 100 may download. Once the data and or executables have been downloaded, the subscriber 100 using the function keys 207 and/or the keypad 206 may retrieve the information. The subscriber may view the data on the display 202 or, in the alternative, may run the executable so that, for example, the newly acquired operating system or feature may be installed in the CPE 101. The function keys 207 which may be "soft" keys (program encoded keys) may include a download feature, an install feature, an activate DTMF or VRU feature, speed dialing feature and or any other such feature (s) that may be required for the subscriber to effectively download data and/or executables into their PSD 106. In a dumb telephone environment, the user of a service according to the present invention may use predetermined sequences of keys to control their PND (110).

In embodiments of the present invention, the memory may further store the personal rule-base 105 that the subscriber 100 may edit to regulate how information is received from the operator 103 and/or directly from the PND 110 in the network. Once the rule-base 105 has been edited and executed, in embodiments of the present invention, it may be downloaded into the RAM 203 or flash memory 204 where the CPU 201 may access the rule-base 105 or rules to apply to the information received from the communications module 208. Embodiments of the present invention may utilize data caching to quickly access information and/or numbers frequently used by the subscriber 100. Subscriber 100 may predefine one of the function keys 207 to access the system cache (not shown) and access the stored information.

As discussed above, the communications module 208 may establish the communications protocol for permitting effective transmission and reception of information from, for example, the operator 103 and/ or the network to the subscriber's CPE 101. If the subscriber's PND 110 including the PSD 106 and/or personal rule-base 105 are located in a remote location, relative to the operator 103, the communications protocol may facilitate the downloading of executables and or data to the subscribers, for example, CPE 101. The protocol may establish communications, for example, between the operator 103 and the subscriber's 100 CPE 101 device to permit the operator 103 to transmit the requested data and/or executables to the subscriber's 100 CPE 101. The communications for the established protocol may be in the form of analog or digital signals depending on the type of CPE 101 and/or the network. The communications data may be transmitted and/or received utilizing in-band or out of band signaling. The function keys 207 may be separately represented by specific analog frequencies or tones or instead by one or more bits/bytes of digital data. Once the communications protocol has been established, the user may select the required function by way of function keys 207. The communications module 208 of the transmitting device may send the appropriate signaling data to, for example, the operator 103 or the device 116 in communication with the PND 110 to begin transmission of the desired data and/or executables. The communications module 208 may interpret the data and/or executables and the information may be stored in memory 206 by the CPU 201. The flash unit 204 may store the communications protocol enabling the CPE 101 to communicate directly with the PND 110 and/or download the requested information. The flash unit 204 may be easily updated for additional functions and/or higher protocol versions as required.

Figure 3:
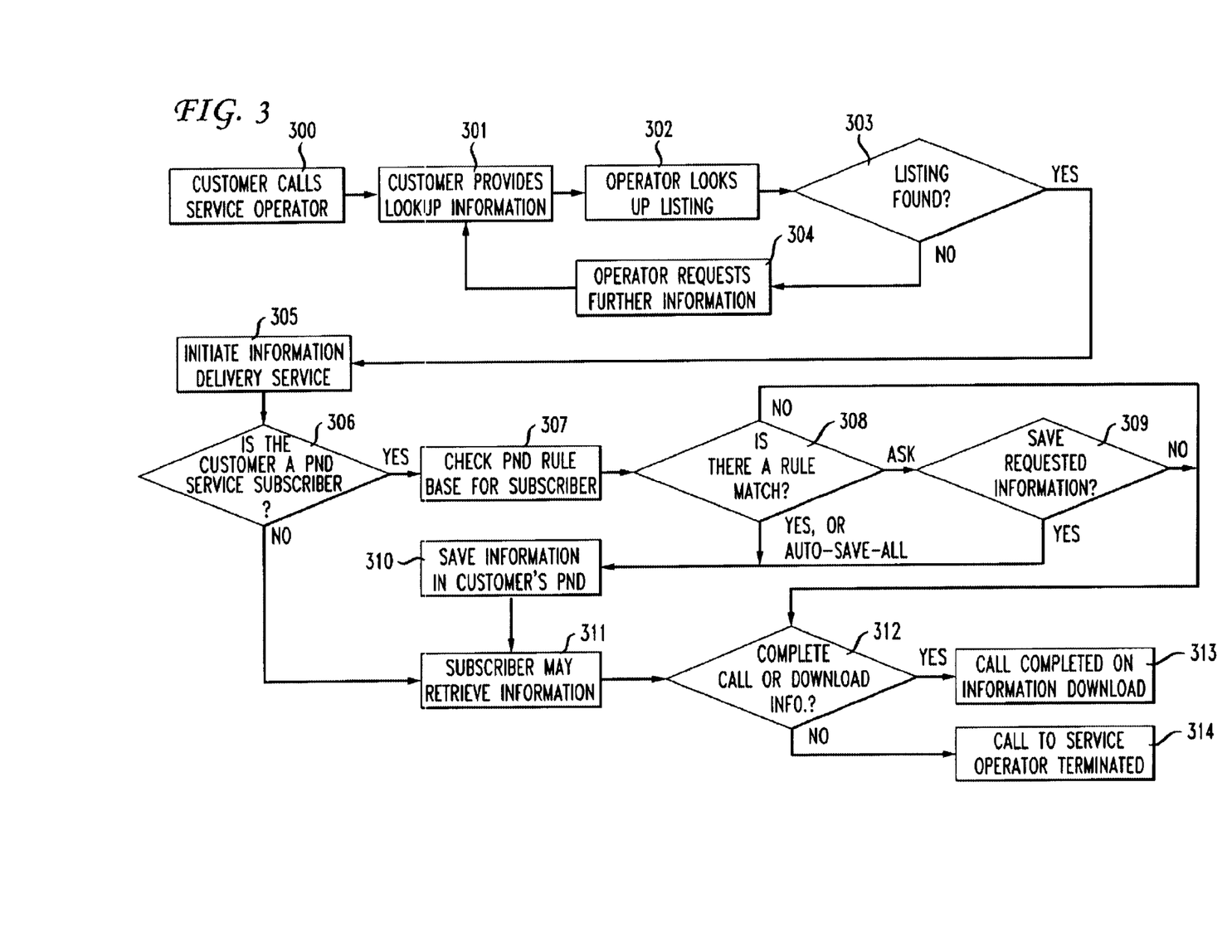
FIG. 3 is a flow chart relating to an embodiment of the present invention.

FIG. 3 relates to an embodiment of the present invention. A customer or caller calls a service operator to request a telephone number of a called party or desired executable, as shown in step 300. The caller provides the appropriate lookup information to identify the called party or the executable, as shown in step 301. The lookup information may include, for example, the name, city and/or state of the called party or any suitable information to look up the called party (e-mail address in an Internet embodiment). If the subscriber wants to down load a game or other executable, the subscriber may provide the version of the desired game or executable. The service operator (machine or human) looks up the listing and if the listing is not found, the operator may verify the information and/or may request further information from the user, as shown in steps 302–304. If the listing is found, the operator initiates an information delivery process, as shown in step 305. This may subsequently be followed by a determination whether the caller is a PND service subscriber, as shown in step 306. If the caller is not a PND service subscriber, the requested information is provided to the caller, as shown in step 311. If the subscriber requested the number of a called party, the subscriber may be permitted to automatically complete the call and, at optionally an additional charge, the call is completed to the called party, as shown in steps 312–313. If, however, the subscriber does not wish to have the call automatically completed, the call to directory service is terminated, as shown in step 314.

If, in step 306, it is determined that the caller is a PND service subscriber, then, in embodiments of the present invention, the system checks the subscribers PND rule-base, as shown in step 307. As indicated earlier, the subscriber's PND rule-base may indicate how the requested information should be processed. As shown in step 308, the system of the invention checks the rules in the rule-base and verifies a predetermined rule match. If the subscriber has pre-defined a rule, for example, that all residential information requested from service operator be appended to the subscriber's PND, then if there is a rule match, the requested information will be delivered and saved to their PND, as shown in step 310. Another choice at this point, if the subscriber's telephone is not intelligent, is to have a rule saying that the information be maintained in network memory. If the subscriber's rule-base indicates that the subscriber wants to be prompted on a per-transaction basis, the system asks the subscriber whether the requested information should be saved in the subscriber's PND, as shown in step 309. If the subscriber selects "yes" to the option to save the information in their PND, then the requested information will be delivered and saved to the subscriber's PND, as shown in step 310. The information may be telephone numbers, addresses, applications, games, additional features and/or other executables. If the subscriber chooses "no," (i.e., not to save the information), for example, the call may be completed without storing the information, as shown in step 312. In embodiments of the present invention, if the information is not stored, for example, data or executables may be lost or may be stored temporarily and deleted after a predetermined period of time (e.g., one hour, one day, one week, two weeks, etc.)

After the information has been saved in the subscriber's PND, the subscriber, as shown in step 311 can retrieve the stored information. As indicated earlier, the subscriber can choose to automatically complete the call or download the information and the call is completed to the called party or the information is downloaded into the CPE, as shown in steps 312–313. If, however, the subscriber does not desire automatic completion of the call or download the information, the call to the service operator is terminated, as shown in step 314. Under embodiments of the present invention, after the call to service operator is terminated, the subscriber of the PND service can complete the call using the newly acquired telephone number directly from their personal directory stored in the CPE, as will be discussed in more detail below, or from the PND. If the subscriber downloaded a game or other executables into their PND, the subscriber may download this information into their CPE at any convenient time. In alternative embodiments of the present invention, the information, game and/or executables may bypass the subscriber's 100 PND 110 and may be downloaded directly into the subscriber's 100 CPE 101. This may be accomplished via a rule in rule base 105 or, alternatively in embodiments of the present invention, via a personal configuration program file stored and/or processed by the server 115. The personal configuration file may contain higher end information for the subscriber 100, for example, identity, address, number and types of CPE 101 owned by the subscriber 100, billing information, system preferences and/or other administrative functions or preferences that require higher level management. Optionally, the personal configuration file may be stored in the PND 110 and accessed by the server 115 as required.

Referring again to FIG. 3, step 309, if the subscriber does not want to save the requested information in their PND, the requested information may be provided directly to the subscriber and the subscriber can choose to automatically complete the call or download information, as shown in steps 311–313 or terminate the call to the service operator, as shown in step 314. Accordingly, the subscriber's PND has not been appended with the requested number of the called party, and the subscriber will have to note the number via any conventional method available to the subscriber or call directory services again, if the called party needs that number later. The alternative is for the user to select having the number stored in the network for later use or downloading. The number can be given a nickname or voice print tag such as "Mom" and stored for temporary use from a dumb communications device or for later downloading to an intelligent communications device.

Figure 4:
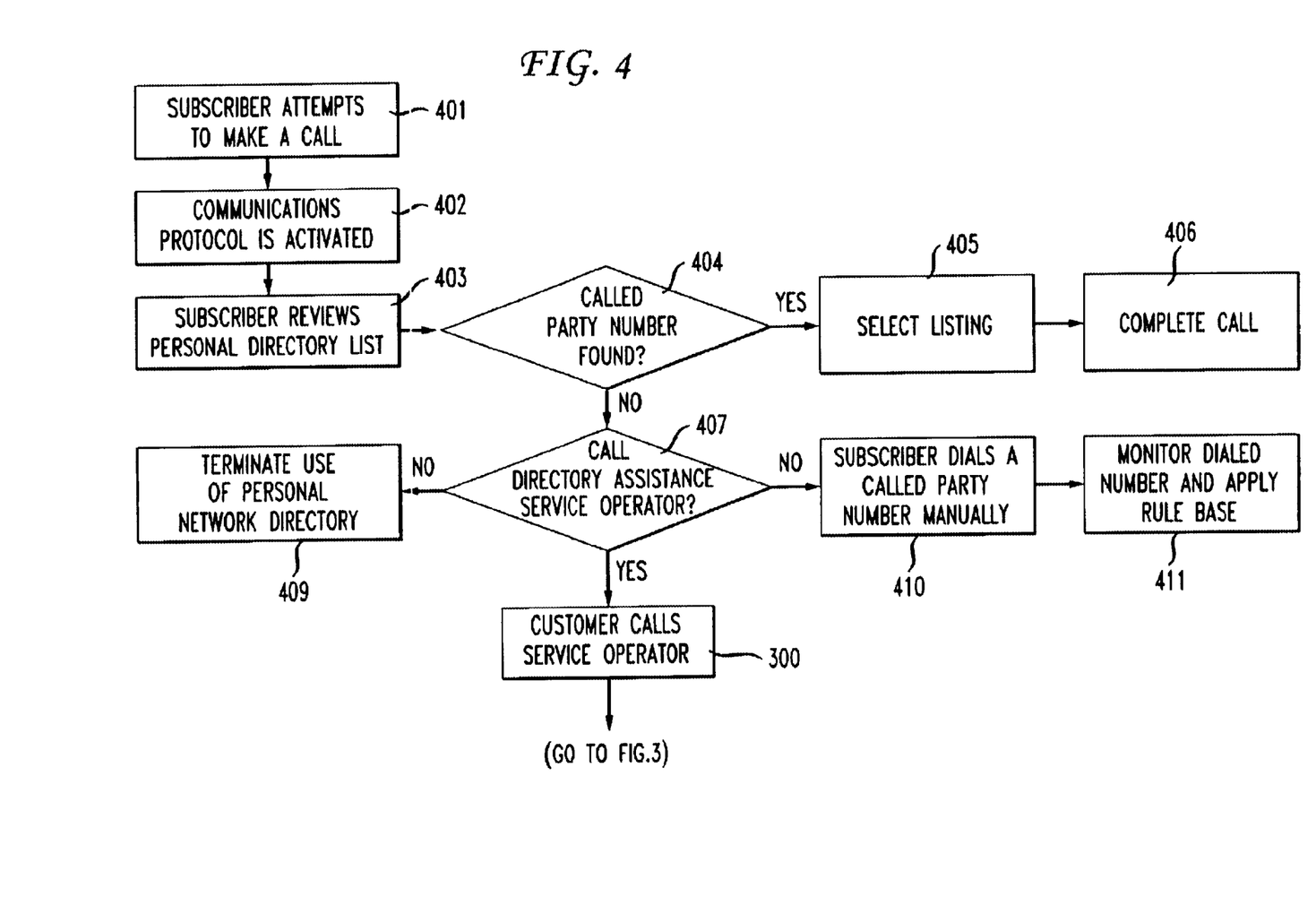
FIG. 4 is a flow chart relating to another embodiment of the present invention.

FIG. 4 relates to another embodiment of the present invention. As shown in step 401, PND service subscriber goes off hook or attempts to make a call via their CPE which may be their cell or digital phone, work phone, home phone or personal computer. The communications protocol is activated and the subscriber's PDL is displayed on the user's CPE display, as shown in step 402. The subscriber reviews their PDL to find the number of a called party, as shown in step 403. Under embodiments of the present invention, the subscriber may have previously stored the number of the called party with a voice print tag in the subscriber's voice, for example, "Mom." As discussed earlier, the subscriber's voice print tag may be encoded and stored with the associated information in the subscriber's PDL. Thus, the caller may retrieve the desired number by spelling out the called party's name on the key pad, scrolling or searching through the PDL or by saying "call Mom" into the CPE's microphone. In the latter case, the system of the present invention may recognize the command "call" and the voice print tag "Mom" and search for the matching voice print tag previously encoded and stored in the PDL. Once a match for the voice print tag is found, the system may proceed to effect the command on the voice print tag and complete the call. In embodiments of the present invention, the subscriber 100 may be able to activate and/or deactivate voice command processing by, for example, the key pad 206, one of the function keys 207 and/or a voice command such as "turn voice command on" or "turn voice command off" and or any other suitable voice command. As indicated earlier, such administrative information may be stored in the subscriber's personal configuration program file.

As indicated earlier, the subscriber's PDL may be located within their CPE or in the alternative, may be located external to their CPE. As shown in steps 404–406, if the called party number is found in the subscriber's PDL, the subscriber can select the number by any method described above and the call is completed. If, however, the number of the called party is not listed the subscriber's PDL, the subscriber may be invited to dial or the system may automatically dial directory assistance, as shown in step 407, which may be the network directory assistance or a service operator according to the present invention. If the subscriber chooses to call directory service assistance and/or the service operator, then the call may proceed as shown in step 300 of FIG. 3. If however, the subscriber chooses not to call directory assistance, the subscriber's call will be terminated, as shown in step 409.

As shown in steps 410 and 411, if the subscriber dials a called party number manually, the system of the present invention may monitor the dialed number and apply the subscriber's rule-base. As discussed earlier, if the subscriber's rule-base indicates, for example, that all outgoing calls are to be appended to the subscriber's PDL, then the subscriber may be invited to enter the information associated with the number dialed either before the call is completed or after it is terminated. If however, the rule-base indicates that numbers are to be appended on a per transaction basis, the subscriber may be asked whether the number should be saved in the PDL or otherwise disregarded. In alternative embodiments, the subscriber may have a rule that the subscriber be asked, when a local number is dialed in a roamed area, whether the subscriber desires that the local number be saved in the subscriber's PDL 152 and/or PND 110. In alternative embodiments, the subscriber 100 may, for example, predefine expiration dates for certain numbers and/or programs so that the numbers and/or programs can be automatically deleted from the PDL 152 and/or PND 110 at the predefined expirations dates.

In embodiments of the present invention, the PND may be accessed, for example, by a unique sequence of digits not recognizable as a telecommunications terminal address such as #*Tom for accessing Tom's PND. The PND thus stored may be, for example, a personal directory of names and device addresses learned over time by observing Tom's calling patterns or calls to Tom in accordance with Tom's rule-base. In alternative embodiments of the present invention, the subscriber 100 may define one of the function keys 207 or a phone number and a personal identification number (PIN) to access their PND 110. In alternative embodiments of the present invention, function keys 207 may be pre-defined the manufacturer of the device and/or may be pre-programmed by the service provider.

Figure 5:
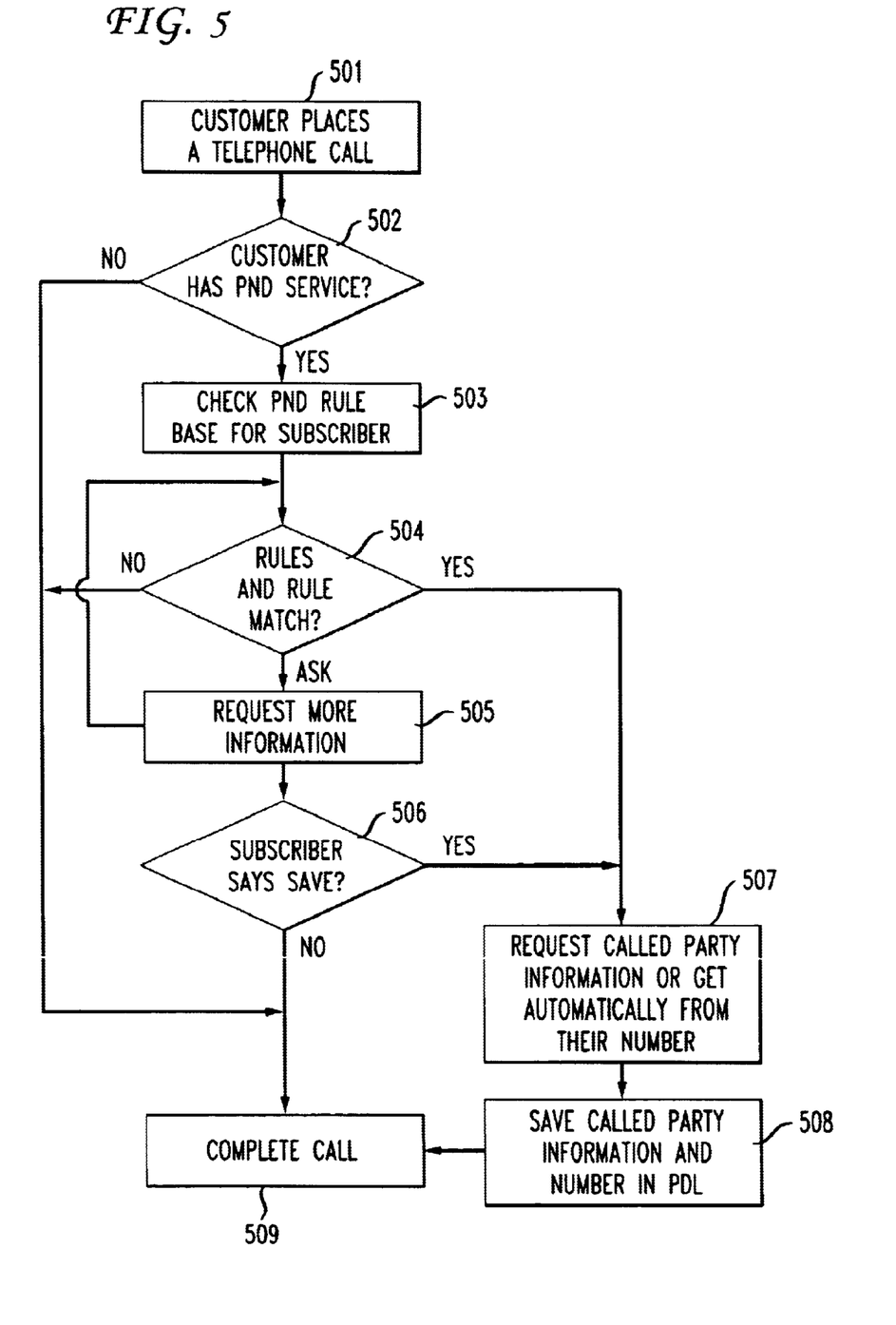
FIG. 5 is a flow chart relating to another embodiment of the present invention.

FIG. 5 relates to yet another embodiment of the present invention. As shown in step 501, a caller dials the telephone number for a called party. The system in accordance with an embodiment of the present invention may begin PDL call processing by determining whether the caller is a PND service subscriber, as shown in step 502. This verification may be based on the subscriber's 100 CPE 101 ANI or if the subscriber is at, for example, a pay phone, the subscriber may have a credit card or a calling card or a PIN to verify status as PND service subscriber, and identify themselves. If the caller is not a PND service subscriber, the communications protocol is not activated and the call may be completed to the called party based on the dialed number, as shown in step 509. If, however, the caller is a PND service subscriber, then the communications protocol is activated and system checks the subscriber's PND rule-base, as shown in step 503. As shown in step 504, the system checks the rules in the rule-base and verifies a predetermined rule match. If the subscriber has pre-defined a rule, for example, that all directly dialed outbound numbers should be appended to the subscriber's PND, then the system may request called party information from the subscriber or may automatically get the called party's information from the called party's number, as shown in steps 504 and 507. The called party information may be automatically determined based on the called party's number so that the subscriber need not provide such information to the system. The called party information may include the name, address, number type (i.e., residence or business number), (e-mail address) and/or any other suitable information for corresponding the dialed number with the called party. After the called party information has been received, the dialed number and corresponding information is saved in the PDL of the subscriber's PND, as shown in step 508. As shown in step 509, the call is completed as previously dialed. Although, a sequential action is shown in FIG. 5 and described above, it is to be understood, that PDL call processing may occur, for example, in parallel, directly before the outgoing call is completed, during the call, or subsequently after or substantially after the call has been terminated, and/or any combination there of.

In embodiments of the present invention, a subscriber may have a rule in their PND rule-base that requires further information. This may include, for example, whether the dialed number is a residential or business number before the number is appended to the subscriber's PND. Accordingly, the system may request the additional information. In alternative embodiments, if the subscriber's rule-base indicates that the subscriber wants to be prompted on a per-transaction basis, the system asks the subscriber whether the dialed number should be saved in the subscriber's PND, as shown in step 506. If the subscriber selects "yes," then, as described earlier, the system may request called party information from the subscriber or get such information automatically from the called party's number, as shown in step 507. After the called party information has been received, the dialed number and corresponding calling party information is saved in the directory list of the subscriber's PND, as shown in step 508. A shown in step 509, the call is completed as previously dialed.

Figure 6:
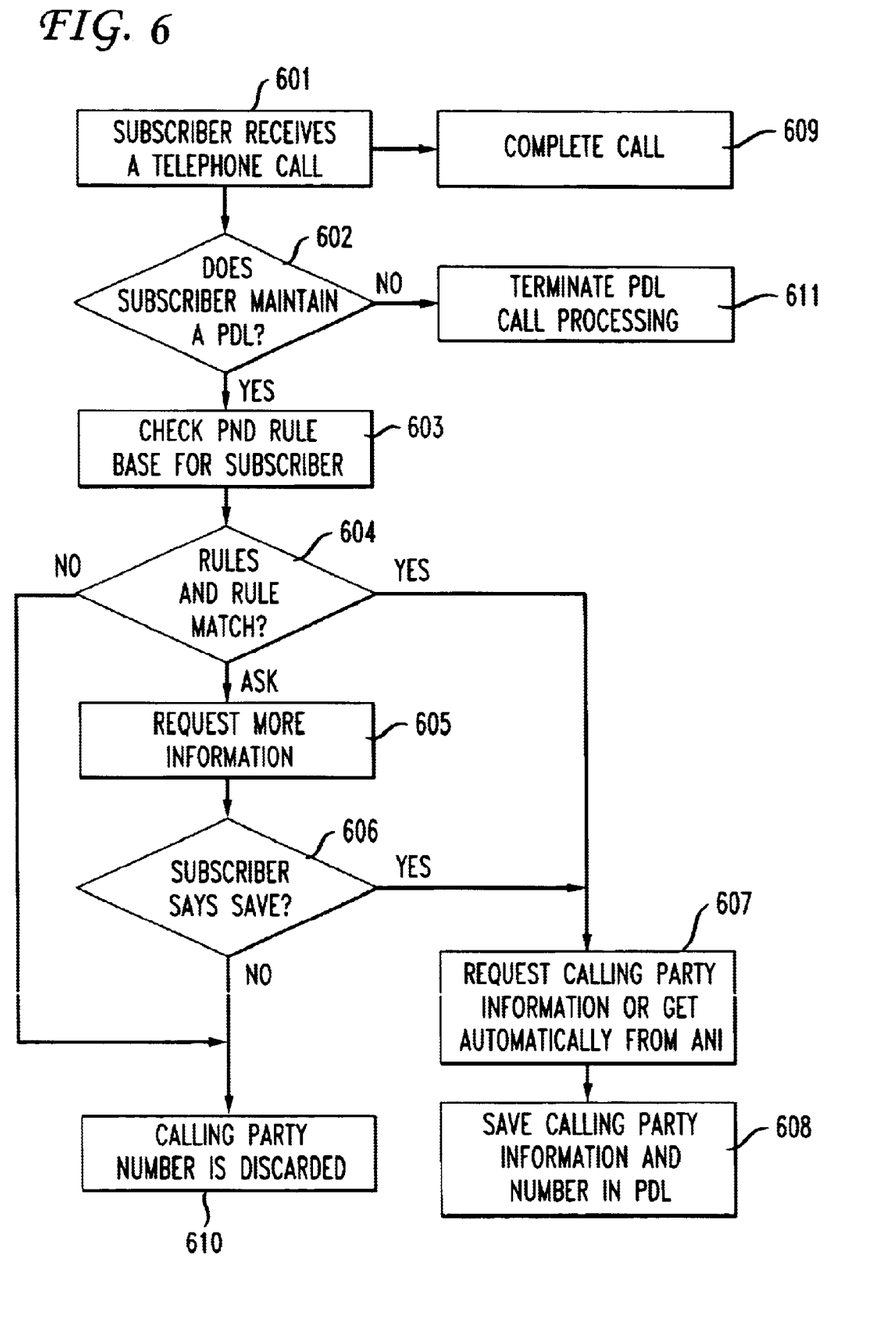
FIG. 6 is a flow chart relating to another embodiment of the present invention.

FIG. 6 relates to another embodiment of the present invention. As shown in step 601, a PND service subscriber receives an incoming call at any one of their CPE. In a preferred embodiment, the call to the subscriber is completed, as shown in step 609. It is to be understood that call completion may comprise, for example, that the subscriber answers the call, the subscriber's voice mail or answering service answers the call, and/or the call is forwarded to the subscriber. In parallel, PDL processing in accordance with embodiments of the present invention may begin, as shown beginning on step 602. In alternative embodiments of the present invention, PDL processing may occur directly before the incoming call is completed, during, subsequently after or substantially after the incoming call has been terminated and/or any combination thereof The system in accordance with an embodiment of the present invention may determine whether the subscriber maintains a PDL, as shown in step 602. If the subscriber does not maintain a PDL, the PDL call processing may be terminated, as shown in step 611. If the subscriber maintains a PDL, while the subscriber or their answering service, for example, is attending to the incoming call, the communications protocol is activated and system checks the subscriber's PND rule-base, as shown in step 603. As indicated above, the protocol activation and rule-base checks may occur in the background parallel to the call being completed. As shown in step 604, the system checks the rules in the rule-base and verifies a predetermined rule match. If the subscriber has pre-defined a rule, for example, that all incoming calls should be appended to the subscriber's PND, then the system may request calling party information from the subscriber or get such information automatically from the calling party's ANI, as shown in steps 604 and 607. The calling party information may be determined based on the calling party's ANI and automatically appended to the subscriber's PDL. The calling party information may include, for example, the name, address, number type (i.e., residence or business number), (e-mail address) and/or any other suitable information for the calling party. After the calling party information has been received, the calling party's number and corresponding information is saved in the PDL of the subscriber's PND for future use, as shown in step 608.

In embodiments of the present invention, a subscriber may have a rule in their PND rule-base that requires further information. This may include, for example, whether the incoming call is residential or business number or requests to add a voice print tag to the number before the number is appended to the subscriber's PDL. This request is preferably done after the subscriber has spoken and has terminated the call with the calling party. Alternatively, such request may be made before or immediately after the call is made or at a later time. Accordingly, the system may request the additional information and append the PDL accordingly. In alternative embodiments, if the subscriber's rule-base indicates that the subscriber wants to be prompted on a per-transaction basis, the system asks the subscriber whether the information for the calling party should be saved in the subscriber's PDL, as shown in step 606. This inquiry, by the system, is preferably done after the subscriber has spoken and/or otherwise terminated the call with the calling party. Alternatively, such inquiry may be made before the call is completed or immediately after the call is terminated or at a later time. If the subscriber selects "yes," then, as described earlier, the system may get calling party information from the subscriber or the ANI, as shown in steps 607. After the calling party information has been received, the calling party's number and corresponding information is saved in the PDL of the subscriber's PND for future use, as shown in step 608. If the subscriber selects "no," calling party number may be discarded, as shown in step 610. In embodiments of the present invention, the calling party number may be stored temporarily or a predetermined period of time and then discarded.

While particular embodiments of the present invention have been described and illustrated, it should be understood that the invention is not limited thereto since modifications may be made by persons skilled in the art. The present application contemplates any and all modifications that fall within the spirit and scope of the underlying invention disclosed and claimed herein.

I claim:

1. A network method for maintaining a personal directory by a subscriber in a network, the method comprising the steps of:

receiving a communication at a service operator from a calling party, the communication requesting called party information;

determining whether one of the calling party or the called party is a personal directory service subscriber; and if the calling or called party is a personal directory service subscriber, the network accessing a rule-base for the subscriber said rule-base containing a plurality of rules for controlling the requested information, said rule-base further capable of identification of a plurality of applications software packages contained within a terminal apparatus of said subscriber and for obtaining storage in said personal directory updates for said software application packages, said rule-base authorizing one of either (1) downloading the requested called party information into a personal directory of a communications device of said subscriber, said downloading comprising checking a rule-base for the subscriber and if there is a rule match, appending the personal directory based on at least one of the plurality of rules in the rule-base or (2) storing said requested called party information in a network personal directory.

2. A network method for maintaining a personal network directory by a subscriber of a personal network directory service in a network, the method comprising the steps of:

receiving a communication at a service operator from the subscriber of the personal directory service, the communication requesting information, wherein the requested information comprises at least one of a plurality of phone numbers, physical addresses, e-mail addresses, URLs, operating systems, games, applications and executable programs;

locating the requested information from a master storage device;

forwarding the requested information to a personal directory list located in one of a personal directory of a communications device of the subscriber or in the subscriber's personal network directory, the subscriber's personal network directory having a personal directory rule-base for the subscriber, said rule-base for controlling flow of the located information into the subscriber's personal network directory;

checking the personal directory rule-base for the subscriber, said rule-base containing a plurality of rules for controlling the requested information and if there is a rule match, appending the personal network directory based on at least one of the plurality of rules in the personal network directory rule-base; and downloading the located information into the subscriber's personal network directory, the located information comprising at least one of the plurality of phone numbers, physical addresses, e-mail addresses, URLs, operating systems, games, applications and executable programs.

3. A network method for maintaining a personal network directory by a subscriber of a personal network directory service in a network, the method comprising the steps of:

receiving a communication at a service operator from the subscriber of the personal directory service, the communication requesting information, wherein the requested information comprises at least one of a plurality of phone numbers, physical addresses, e-mail addresses, URLs, operating systems, games, applications and executable programs;

locating the requested information from a master storage device;

forwarding the requested information to a personal directory list located in one of a personal directory of a communications device of the subscriber or in the subscriber's personal network directory, the subscriber's personal network directory having a personal directory rule-base for the subscriber, said rule-base for controlling flow of the located information into the subscriber's personal network directory;

checking the personal directory rule-base for the subscriber, said rule-base containing a plurality of rules for controlling the requested information and if there is a rule match, appending the personal network directory based on at least one of the plurality of rules in the personal network directory rule-base; and downloading the located information comprising at least one of the plurality of phone numbers, physical addresses, e-mail addresses, URLs, operating systems, games, applications and executable programs into at least one of the subscriber's personal network directory or into the subscriber's communications device via a communications protocol established between the service operator and the subscriber's communications device, said device for storing and executing at least one of the plurality of phone numbers, physical addresses, e-mail addresses, URLs, operating systems, games, applications and executable programs.

* * * * *